(12) United States Patent
Van Campenhout et al.

(10) Patent No.: US 6,898,845 B2
(45) Date of Patent: May 31, 2005

(54) METHOD FOR MANUFACTURING HYBRID ELECTRONIC CIRCUITS FOR ACTIVE IMPLANTABLE MEDICAL DEVICES

(75) Inventors: Yves Van Campenhout, Villeneuve-Saint-Georges (FR); Dominique Gilet, Antony (FR); Thierry Legay, Fontenay-les-Briis (FR)

(73) Assignee: ELA Medical S.A., Montrouge (FR)

( * ) Notice: Subject to any disclaimer, the term of this patent is extended or adjusted under 35 U.S.C. 154(b) by 582 days.

(21) Appl. No.: 10/056,843

(22) Filed: Jan. 17, 2002

(65) Prior Publication Data

US 2002/0147478 A1 Oct. 10, 2002

(30) Foreign Application Priority Data

Jan. 19, 2001 (FR) .............................................. 01 00726

(51) Int. Cl.[7] ............................ H05K 3/36; H01L 23/02
(52) U.S. Cl. .............................. 29/830; 29/831; 29/832; 29/835; 29/841; 257/668
(58) Field of Search .......................... 29/830, 831, 832, 29/835, 841; 257/668, 774, 672, 673; 607/36, 38

(56) References Cited

U.S. PATENT DOCUMENTS

| 3,690,325 | A | | 9/1972 | Kenny ..................... 128/419 R |
|---|---|---|---|---|
| 4,246,595 | A | * | 1/1981 | Noyori et al. ............... 257/668 |
| 4,784,872 | A | | 11/1988 | Moeller et al. ............... 427/96 |
| 5,159,751 | A | * | 11/1992 | Cottingham et al. .......... 29/832 |
| 5,252,854 | A | * | 10/1993 | Arita et al. ................. 257/676 |
| 5,434,362 | A | * | 7/1995 | Klosowiak et al. ......... 174/254 |
| 5,461,255 | A | * | 10/1995 | Chan et al. ................. 257/672 |
| 5,782,891 | A | | 7/1998 | Hassler et al. |
| 5,784,264 | A | | 7/1998 | Tanioka |
| 5,879,502 | A | * | 3/1999 | Gustafson ................... 156/292 |
| 5,954,751 | A | | 9/1999 | Chen et al. |
| 5,963,429 | A | | 10/1999 | Chen |

FOREIGN PATENT DOCUMENTS

| EP | 0 923 130 A1 | 6/1999 | ......... H01L/25/538 |
|---|---|---|---|
| LI | CH 689 217 A | 12/1998 | ........... H01L/21/58 |
| WO | WO 99/41786 | 2/1999 | ........... H01L/25/16 |

* cited by examiner

Primary Examiner—Carl J. Arbes
Assistant Examiner—Tai Van Nguyen
(74) Attorney, Agent, or Firm—Orrick, Herrington & Sutcliffe LLP

(57) ABSTRACT

A method for manufacturing a plurality of hybrid electronic circuits for active implantable medical devices and circuits made by the process. The process includes the following stages: a) preparing a collective plane plate-substrate (10) carrying on a first surface a pattern of contact areas (16) for chips and, on a second surface (the back), a pattern of metallization areas for components, with a repetition of the same patterns for a corresponding plurality of circuits to be made from said substrate; b) gluing on the first surface of the plate of a plurality of chips (12, 14); c) cabling (wiring-bonding) the chips (12, 14) to their corresponding contact areas (16); d) pouring a coating resin over the first surface of the plate to achieve a uniform layer of coating resin (22), e) hardening the resin; f) cutting the plate to form the plurality of individual substrates, with each substrate having on its first surface coated chips, each one of these substrates corresponding to an implantable device individual circuit, and g) mounting SMC components (38, 40, 42) and/or connector elements (44) to the second surface of each individual substrate, so as to complete the electron circuits of the active implantable medical devices.

3 Claims, 2 Drawing Sheets

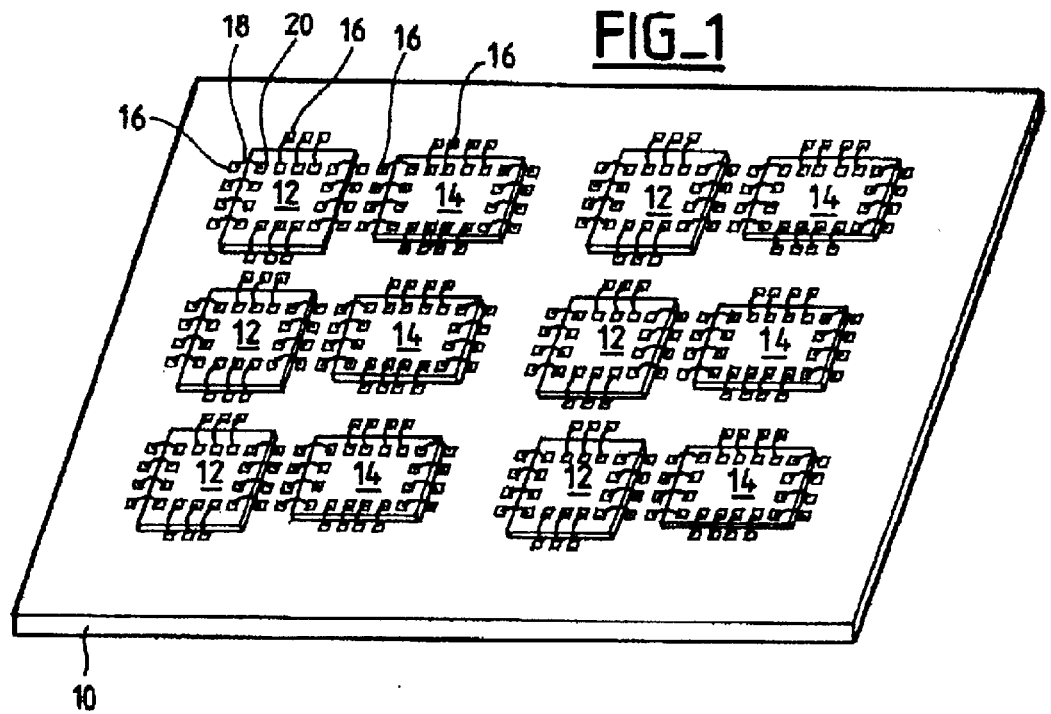
FIG_1
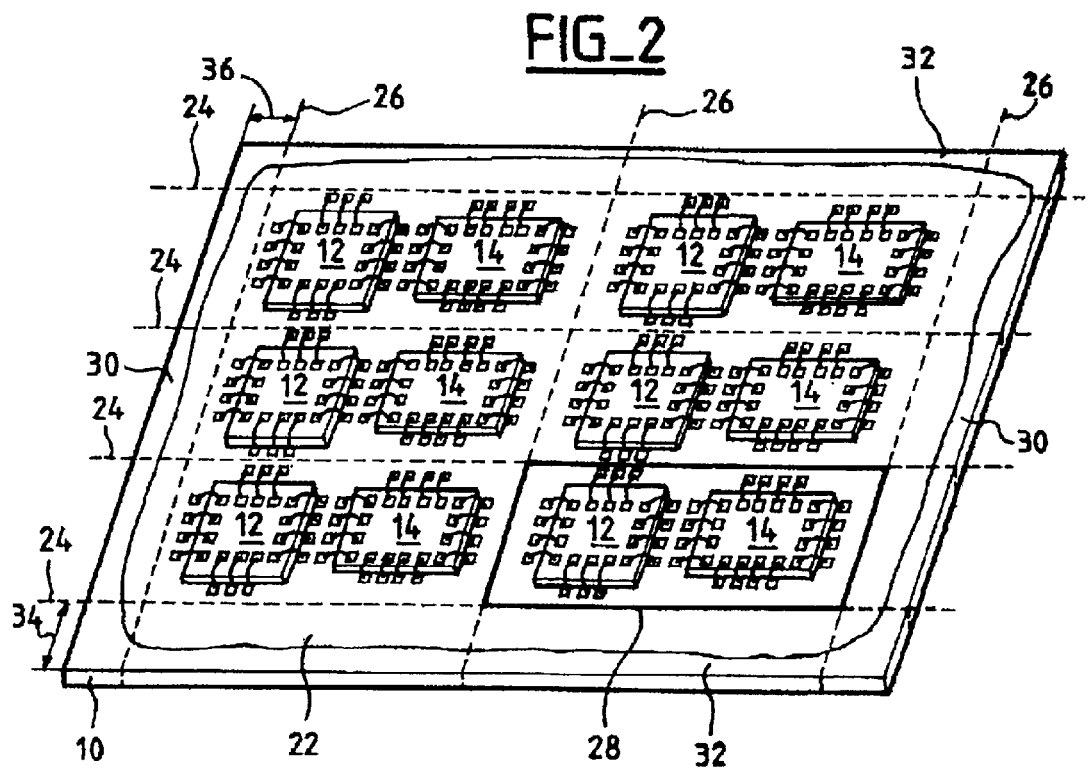
FIG_2

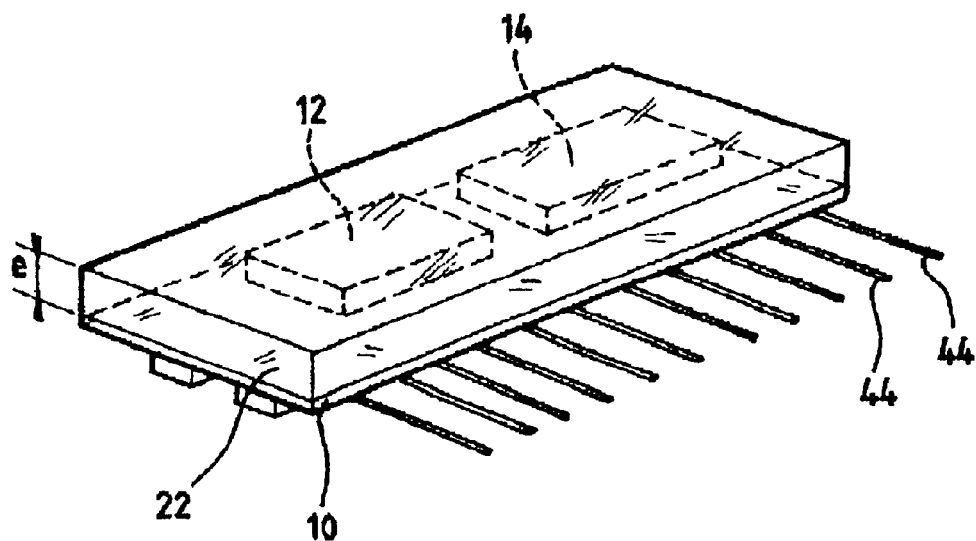
FIG_3
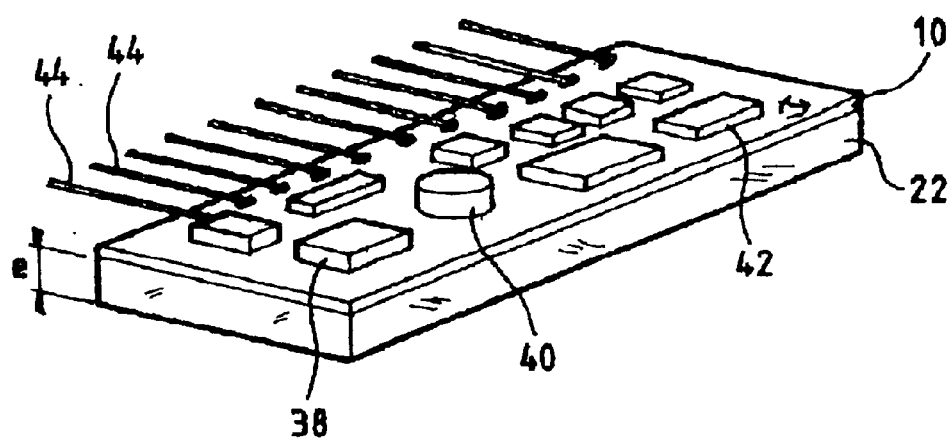
FIG_4

METHOD FOR MANUFACTURING HYBRID ELECTRONIC CIRCUITS FOR ACTIVE IMPLANTABLE MEDICAL DEVICES

FIELD OF THE INVENTION

The present invention relates to manufacturing hybrid electronic circuits for active implantable medical devices. Although described in the context of circuits for implantable pacemakers, one example of an embodiment of the invention, the present invention is applicable in a much more general way to a very large variety of "active implantable medical devices." As those devices are defined by the Jun. 20, 1990 Directive 90/385/CE of the Council of the European Communities, active implantable medical devices include, in addition to pacemakers, defibrillators and/or cardiovertors, neurological devices, diffusion pumps for medical substances, cochlear implants, implanted biological sensors, etc.

BACKGROUND OF THE INVENTION

Active implantable medical devices (hereafter "implantable devices" or "devices") comprise a case containing a power supply and a hybrid circuit board supporting and interconnecting the active and passive components (hereafter an "electronic circuit"). In the case of a pacemaker, an electronic circuit allows for the collection and the analysis of cardiac signals, the generation of stimulation pulses, the memorizing (storage in memory) of various information for medical follow-up, and the control of the various functions of the pacemaker device. A connector head is typically connected to the electronic circuit and provides the electric and mechanical connection to external elements, in particular to the leads or probes for signal collection and/or the application of pulses.

As it is easily understood, these implantable devices require a substantial miniaturization of the electronic circuits, taking into account the limited space available inside the case. More precisely, in addition to different active and passive components generally implemented in surface mounted component ("SMC") technology, as well as connection elements, the electronic circuit carries one or more chips realized by microphotolithography on a semiconductor plate (i.e., a wafer) that is cut into individual chips. These individual chips, as well as the other active and passive components, are typically mounted on a single individual substrate to form the electronic circuit of the device. Because of the different components that are on the substrate, the electronic circuit also is referred to as a "hybrid circuit."

Several techniques are employed today to realize these electronic circuits, but all present their own disadvantages. A first known technique is using a "chip carrier," which is a small individual case at the bottom of which the chip is glued and then cabled by wire bonding. The chip carrier is then sealed by a metal cap and mounted on the substrate of the hybrid circuit. This method is expensive, because it requires an individual treatment of each chip, and requires as many chip carriers as there are chips. It also leads to a large occupied surface, the chip carrier being necessarily larger than the chip it incorporates.

Another known technique is the technique of "assembly in common cavity." The substrate of this hybrid circuit is not flat, but rather comprises a cavity that is sufficiently large to accommodate all of the chips, which are glued and cabled by wire bonding, as in the case of the use of a chip carrier. A common cap then covers the entire cavity. This process has the advantage of treating all the chips of the same hybrid circuit simultaneously, but it does not allow a collective treatment of several hybrid circuits. Moreover, from the point of view of the occupied surface, the walls of the cavity of the circuit on which the cap is sealed occupy a considerable surface area which is lost. Moreover, the use of a cap of large dimensions leads to a delicate distribution of the constraints (stress) between cap and substrate, and that may lead to an increased weakness of the circuit.

Another technique is known as the "chip-on-board" assembly and concerns gluing the chips on the host substrate, and then, after wiring, covering them individually with a drop or "glob" of protective resin (see in particular U.S. Pat. No. 4,784,872). The chip thus coated by a "glob-top" occupies a relatively larger space on the substrate, because it is necessary to envisage a sufficient marginal area for the natural flow of the drop of the coating resin. Moreover, the cost of the technique is relatively high because it is necessary to treat each chip of each circuit individually. Lastly, the mechanical state of the surface which contains the chips covered by a glob-top is not well controlled and does not allow for a well controlled insertion and placement in an implantable device, where each cubic millimeter is counted.

The international patent publication WO-A-99/41786 describes a technique of coating subsets of a pacemaker circuit, where the subsets are covered collectively by a layer of coating resin before being cut. However, this document teaches only the coating of subsets, which must be then mounted on a common substrate forming the substrate of the electronic circuit of the implant. Moreover, this technique does not permit the board to carry components on two faces, because one of the faces of the subset is reserved for mounting it on the substrate of the electronic circuit.

SUMMARY OF THE INVENTION

The present invention, therefore, proposes a new technique for manufacturing an electronic circuit for an active implantable medical device mitigating the aforementioned disadvantages of the known processes, as well as an electronic circuit realized according to this process.

Broadly, one aspect of the invention concerns a process for manufacturing a plurality of hybrid circuit elements that includes the following stages:

a) preparation of a flat collective plate-substrate comprising, on a first surface (i.e., on one side of the plate-substrate) a plurality of repeating patterns of a contact area for chips and, on a second surface (e.g., a second side opposite the first side), a like plurality of repeating patterns of metallization areas for active or passive SMC components or connector elements, wherein the plurality of repeating patterns of contact areas and metallization areas correspond to said plurality of electronic circuits for implantable devices;

b) gluing on the first surface of the collective plate-substrate a second plurality of chips wherein, each of said electronic circuits for an implantable device has at least one corresponding chip, c) cabling selected ones of the second plurality of chips to the contact areas that are associated therewith, d) pouring a coating resin over the first surface of the collective plate-substrate and forming a coating resin layer having a reasonably uniform thickness, e) hardening the coating resin, f) cutting the collective plate-substrate to form a plurality of individual substrates, each substrate having on its first surface the at least one chip coated with the resin, each individual substrate corresponding to an electronic circuit for an implantable device, and g) mounting at least one of an SMC component and a connector element to the second surface of each individual substrate, so as to form a plurality of the complete electronic circuits for the implantable devices.

Advantageously, in one preferred embodiment, the collective plate-substrate comprises a peripheral marginal area such that, at stage d), the resin poured on spreads out freely by gravity until covering the peripheral marginal area, and, at stage f), the peripheral marginal area is severed off by cutting.

In yet another embodiment, after stage e), it can be envisaged to include a stage of depositing a uniform metal layer on the surface of the hardened coating resin layer.

The invention also is directed to an electronic circuit for active implantable medical device realized by the above mentioned process. This electronic circuit is made of a substrate supporting, on its first surface, one or more chips and, on its second surface, the active or passive SMC components and/or connector elements. On the first surface of the substrate is a layer of coating resin covering (encapsulating) the circuits and chips. This layer is preferably of a uniform thickness and extends from one edge of the substrate to another in two dimensions, such that the substrate has sides (in the third dimension) and its layer of resin extends perpendicular to the surface of the substrate. Thus, once the cutting is done, the electronic circuit is essentially rectangular with reasonably flat, and preferably uniformly flat, top, bottom and side walls (unless of course it is deemed desired to cut individual circuit at an angle other than 90° to the first surface).

BRIEF DESCRIPTION OF THE DRAWINGS

Other features, characteristics and advantages of the present invention will appear to a person of ordinary skill in the art in view of the following description, made with reference to the drawings annexed, in which:

FIGS. 1 and 2 illustrate a collective plate-substrate on which the chips of several implantable device circuits are mounted and cabled, respectively before and after the pouring of the coating resin in accordance with the present invention; and FIGS. 3 and 4 are an elevated perspective view, respectively from the bottom and from the top, of a finished electronic circuit, realized according to a process of a preferred embodiment of the present invention.

DETAILED DESCRIPTION OF THE INVENTION

Primarily, the present invention proposes to realize simultaneously several implantable device electronic circuits on the same collective plate-substrate, to coat with a resin in a single stage the entire surface of the plate-substrate, and then to "individualize" each circuit by cutting the coated collective plate-substrate in order to form the various individual electronic circuits. The cutting may be achieved by slicing (or sawing or otherwise severing the substrate into subsections) as known in the art. The face of the substrate (that surface not having received coating resin) is then equipped with metallizations for the mounting of SMC components, connectors, and the like.

With reference to FIG. 1, a flat collective plate-support 10 is represented, which can be made out of a material in itself known such as a ceramic (e.g., a multilayer ceramic structure), rigid epoxy, etc. The material is selected according to the desired mechanical and electric properties for the electronic circuit. The plate-substrate preferably incorporates the various interconnection conductors for the chips and the other components which it is intended to receive.

In the illustrated example, each electronic circuit comprises two chips 12, 14, each one obtained by microphotolithography and cutting of a semiconductor plate. These chips 12, 14 are then mounted and glued on the collective plate-substrate 10 at about the same time in a first stage of the process. Twelve chips are illustrated in FIG. 1, corresponding to six individual implantable device electronic circuits, all mounted and glued on plate-substrate 10.

A wire bonding process ensures the proper wiring of the various chips, by installation of a thin connection wire 18 connecting the appropriate associated contact area 16 of the pattern formed on plate-substrate 10 to the homologous contact areas 20 located on each chip. Any conventional wire bonding fabrication equipment and process may be used to achieve the desired cabling.

The following stage, illustrated in FIG. 2, concerns pouring a coating resin (or "encapsulation") 22 to flow over the plate-substrate 10 and cover all of the chips and their electric connections.

The resin used is selected according to the mechanical strength properties appropriate for the electronic circuit; it is generally a polymerizable material such as a polyimide, an epoxy polymer, a silicone resin, etc. The resin selected is able to flow or run locally and to be hardened in situ, for example, by exposure to UV or an elevated temperature. In a natural manner, the resin will take a substantially flat profile (e.g., except for the edges) by a combination of the surface tension and forces of gravity. Alternatively, the coating resin flowed onto plate 10 is preferably smoothed by a scraper, which may be done manually or automatically by a machine.

Preferably, after polymerization, the hardened material, although rigid, nevertheless has a sufficient flexibility in order not to generate a stress that will buckle the plate-substrate 10.

On FIG. 2, references 24 and 26 are hatched pinpointing lines delimiting the boundaries of each individual electronic circuit. The solid line reference 28 illustrates the contour of one such an electronic circuit, considered separately with its two chips 12, 14.

Compared to dimensions of the electronic circuits, the dimensions of plate-substrate 10 are selected so as to provide peripheral margin areas 30, 32 sufficient so that the edge of the resin 22 mass reaches the corresponding areas 34, 36 of these peripheral margins. This provides a practically planar (i.e., substantially flat or level) surface over the totality of the area of the various individual electronic circuits. After hardening of the resin, the plate-substrate and its layer of coating resin are cut out (sliced or sawed) according to hatched lines 24 and 26, in order to "individualize" each electronic circuit.

As can be seen on FIGS. 3 and 4, each of the individual circuits presents a free face (the second surface of the illustrated plate-substrate of FIG. 2) comprising metallization areas for mounting thereon active or passive SMC components such as structures 38, 40, 42 and/or connection pins 44 for connection of the individual circuit to the medical implant (FIG. 4).

On the other side or first surface of the plate substrate 10 (FIG. 3), the circuit presents simply a flat and rigid layer 22 of resin having a thickness e (typically approximately 0.8 mm), which completely coats the chips 12 and 14 and seals them to the substrate.

In an alternative embodiment, after hardening of the resin and before cutting plate-substrate 10, it is possible also to deposit of a metal layer over the whole resin surface. Such a metal layer can provide several functions, in particular:

electric shielding (for example, by connecting the metal layer to ground), a shield against the penetration of moisture and chemical contaminants, and/or increased mechanical protection.

The process just described presents many advantages, in particular among them are:

A good density of occupation of the surface of the individual electronic circuits, without a loss of a peripheral margin area for the flow of the resin around each circuit as in the case of the glob-top process. Indeed, in accordance with the preferred embodiment of the invention, the peripheral margin areas is reserved only for the collective periphery of the plate-substrate, and does not affect the individual dimensions of each electronic circuit.

An optimization of cost, because the operations of gluing, cabling or wire bonding and pouring of the resin are common to several circuits: if one realizes N circuits on collective plate-substrate 10, one decreases by a factor N the number of input-outputs from the manufacturing process.

A good flatness of the resin surface (which resin is typically spread out simply by gravity, and optionally assisted by a user). Because of the cutting process, the sides of the circuit can be cut straight, thus offering a good mechanical reference, for a precise and easy positioning on a substrate by automated placement equipment.

A good (hermetic) protection of the chips with respect to the external medium.

One skilled in the art will appreciate that the present invention can be practiced by other than the described embodiments, which are presented for the purposes of illustration and not of limitation.

We claim:

1. A method of manufacturing a plurality of hybrid electronic circuits for active implantable medical devices, comprising:

a) providing a flat collective plate-substrate comprising, on a first surface, a plurality of repeating patterns of a contact area for connection to at least one chip, and a second surface opposite the first surface having the plurality of repeating patterns of a metallization area for receiving at least one of an active SMC component, a passive SMC component, and a connector element, wherein said collective plate-substrate pluralities of contact areas and metallization areas correspond to a plurality of implantable device electronic circuits;

b) gluing on the first surface of the collective plate-substrate a second plurality of chips, wherein each of said implantable device electric circuits has at least one corresponding chip, c) cabling each of said glued chips to an associated contact area, d) pouring a coating resin over said first surface of the plate-substrate, and forming a uniform thickness layer of coating resin, e) hardening the coating resin, f) cutting the collective plate-substrate into a plurality of individual substrates, each substrate having on its first surface at least one glued chip coated by the resin, each individual substrate corresponding to an individual implantable device electric circuit; and g) mounting at least one SMC component and/or a connector element to the second surface of each individual substrate, to form said plurality of electric circuits of the implantable devices.

2. The process of claim 1, wherein the collective plate-substrate further comprises a peripheral marginal area and wherein stage d) further comprises spreading the resin over said peripheral area by gravity, and wherein stage f) further comprises cutting off the peripheral marginal area.

3. The process of claim 1, further comprising, after stage e), depositing a uniform metal layer on the hardened coating resin layer.

* * * * *